United States Patent [19]

Eino

[11] Patent Number: 4,989,083
[45] Date of Patent: Jan. 29, 1991

[54] METHOD OF INSPECTING OBJECTS BY IMAGE PICKUP MEANS

[75] Inventor: Teruo Eino, Hachioji, Japan

[73] Assignee: Olympus Optical Co., Ltd., Tokyo, Japan

[21] Appl. No.: 468,673

[22] Filed: Jan. 23, 1990

[30] Foreign Application Priority Data

Jun. 29, 1989 [JP] Japan .................................. 1-167649
Oct. 30, 1989 [JP] Japan .................................. 1-283497

[51] Int. Cl.⁵ ............................ A61B 1/04; A61B 1/06
[52] U.S. Cl. ....................................... 358/107; 358/98; 358/181; 358/903
[58] Field of Search ................... 358/106, 107, 98, 93, 358/903, 100, 181

[56] References Cited

U.S. PATENT DOCUMENTS

| | | | |
|---|---|---|---|
| 4,621,284 | 11/1986 | Nishioka | 358/107 |
| 4,656,508 | 4/1987 | Yokota | 358/107 |
| 4,725,883 | 2/1988 | Clark, Jr. et al. | 358/100 |
| 4,935,810 | 6/1990 | Nonami | 358/107 |

Primary Examiner—Howard W. Britton
Attorney, Agent, or Firm—Armstrong, Nikaido, Marmelstein, Kubovcik & Murray

[57] ABSTRACT

An inspection method utilizing computer graphics in inspecting a certain part of an object which is being imaged by an image pickup apparatus such as an electronic scope. A computer-graphics picture simulating th eobject picture obtained by the image pickup apparatus is drawn by means of a computer-graphics apparatus. The parameters used for the drawing are varied so as to approximate or equalize the computer-graphics picture to or with the object picture, thereby making it possible for any flaw or the like on the object to be detected with ease by comparing the two picture with each other even if the object has a complicated configuration.

Furthermore, that portion of the computer-graphics picture which corresponds to the inspected part of the object picture is specified, and, by using information on the portion thus specified, inspections on the inspected part, such as measurement of length and examination for discoloration, can be performed.

28 Claims, 10 Drawing Sheets

31 INSPECTED PART

M1 ~ M6

M1 ~ M6

FIG. 11a     FIG. 11b
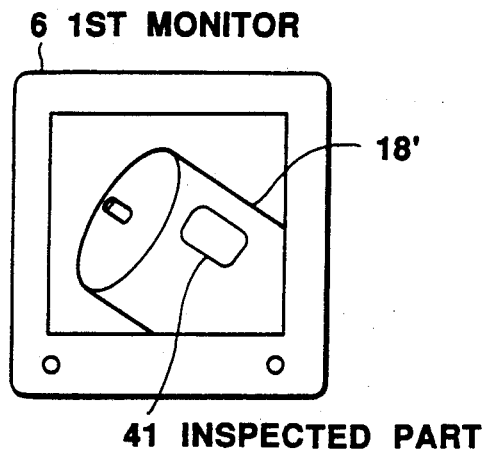
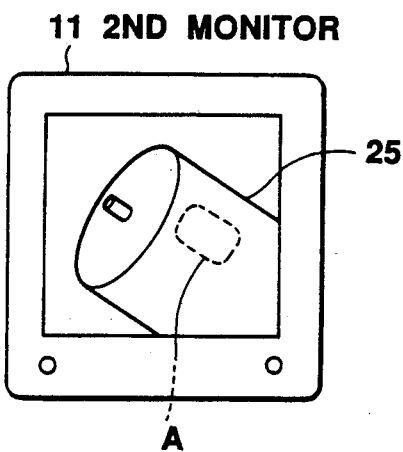
FIG. 12
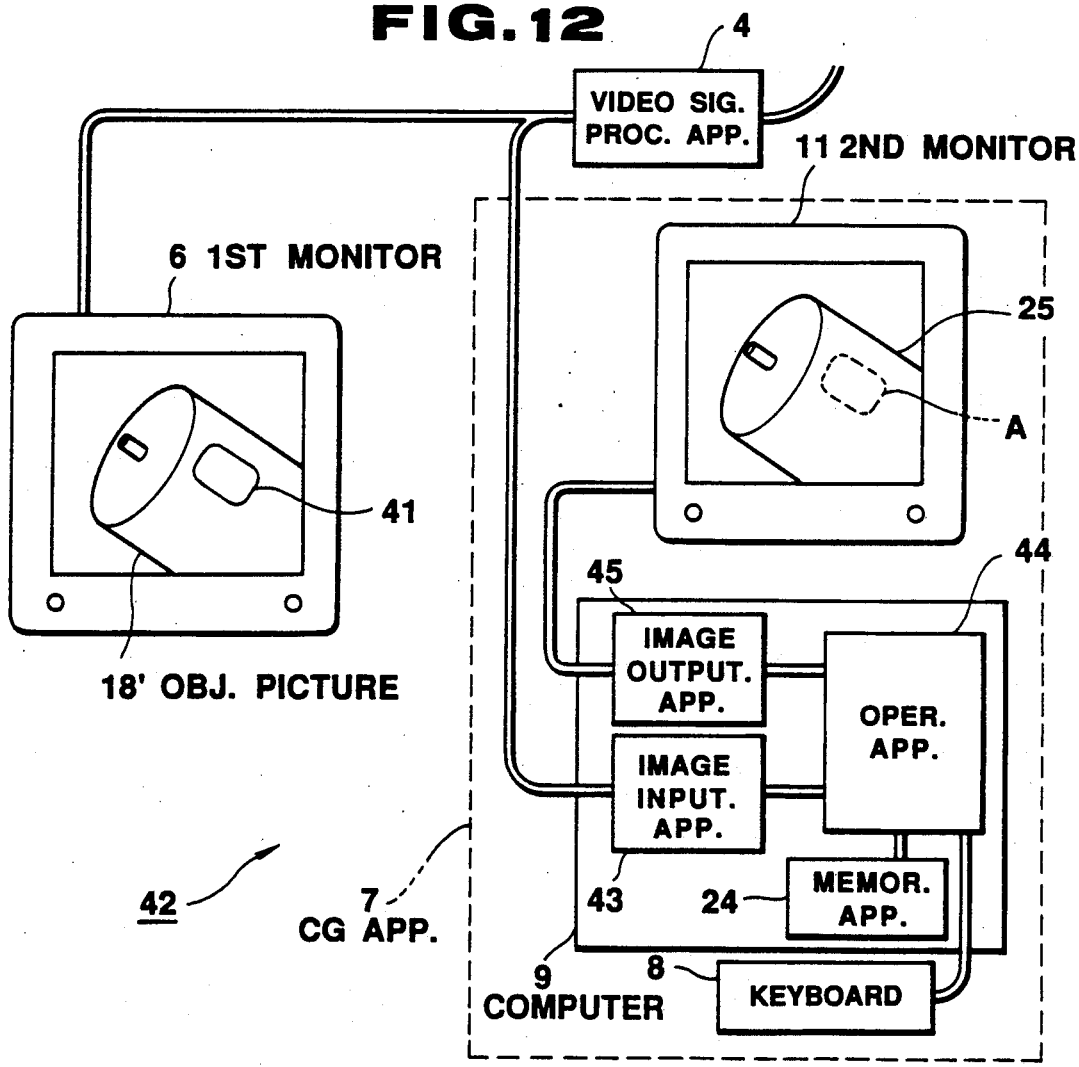

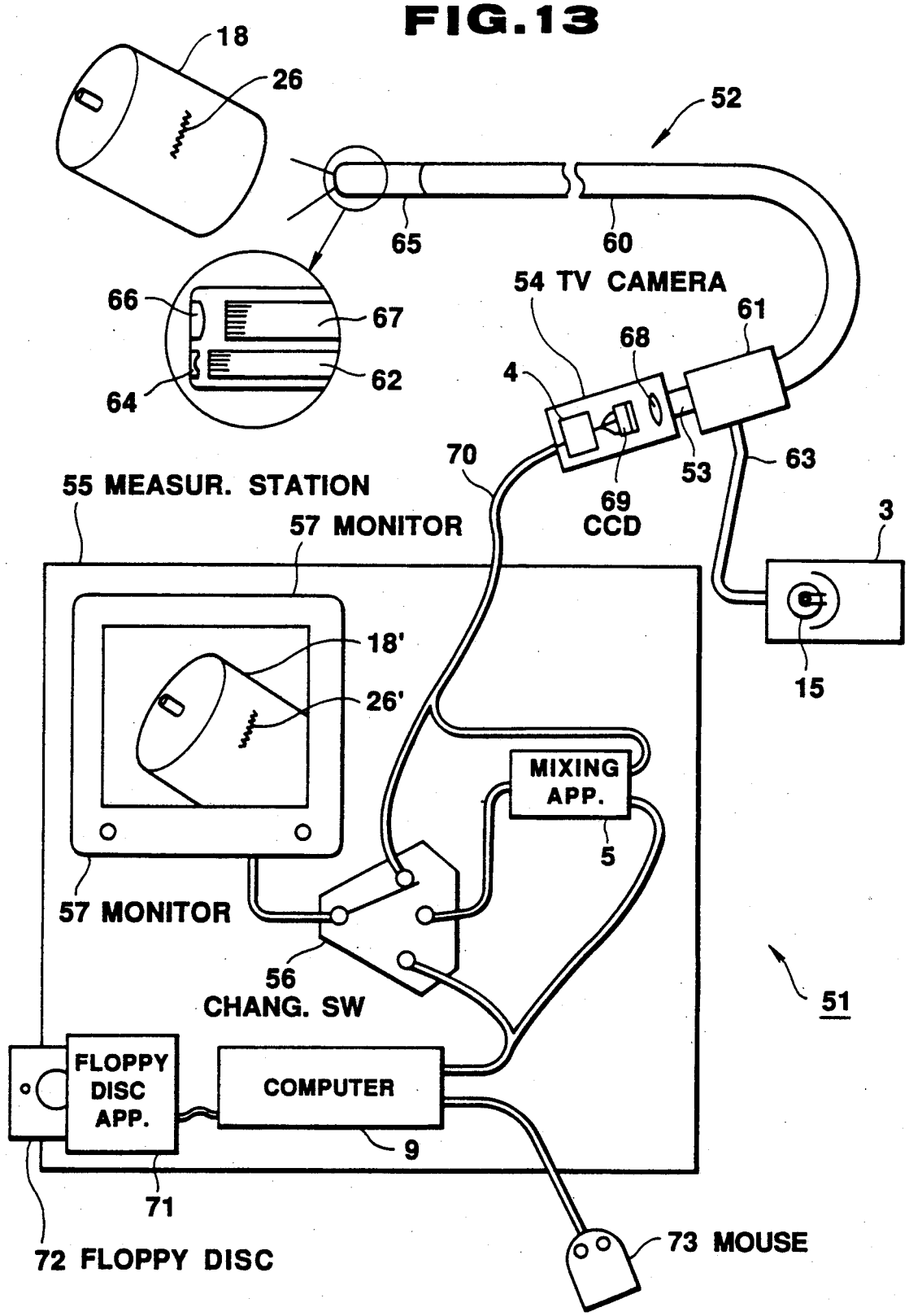

FIG.14a FIG.14b FIG.14c
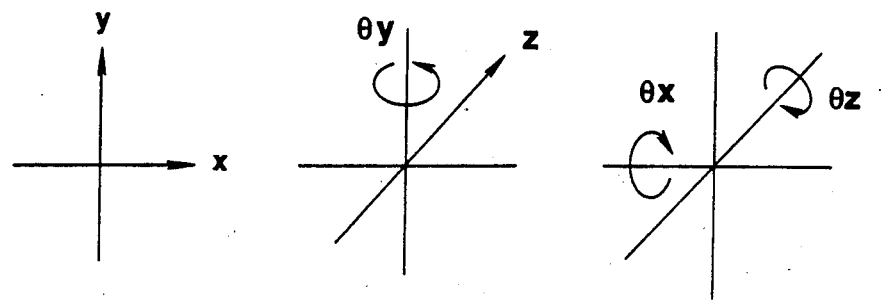
FIG.15
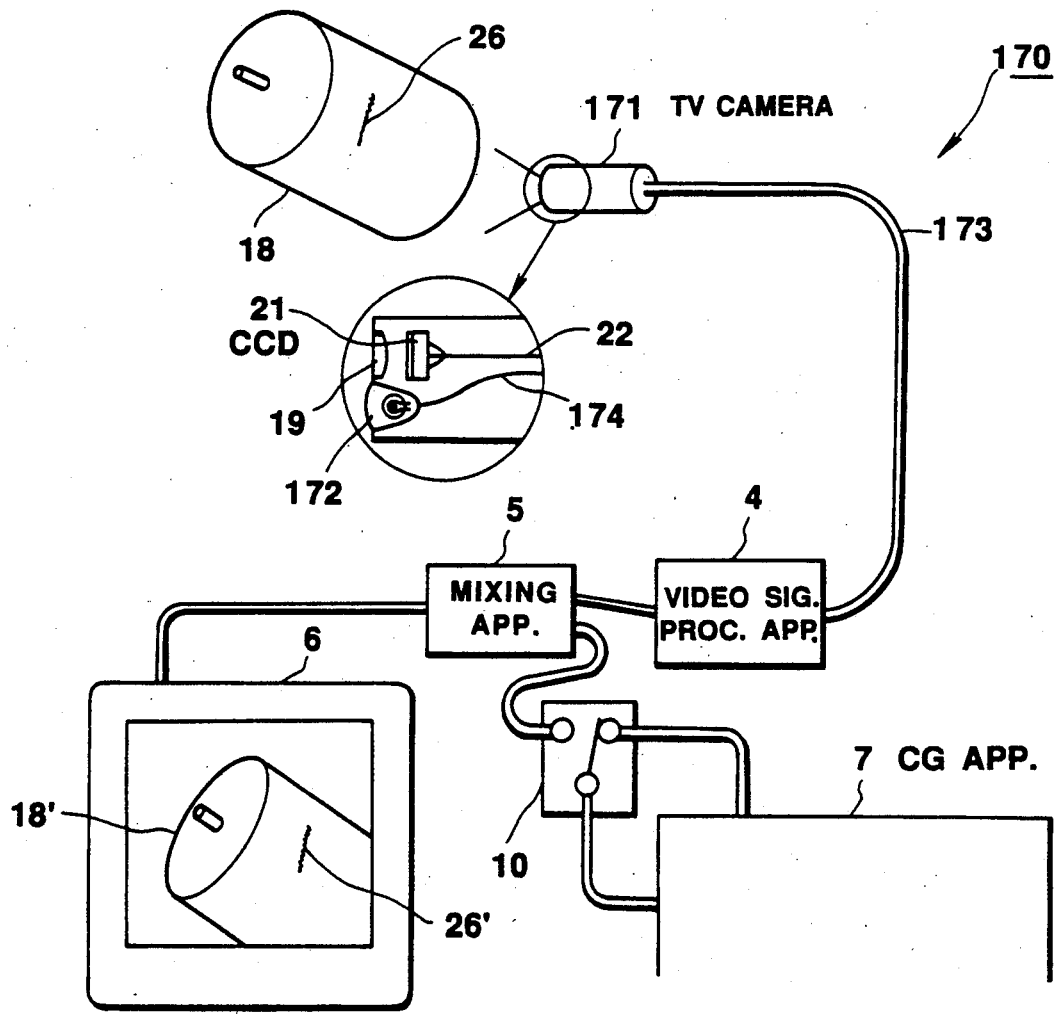

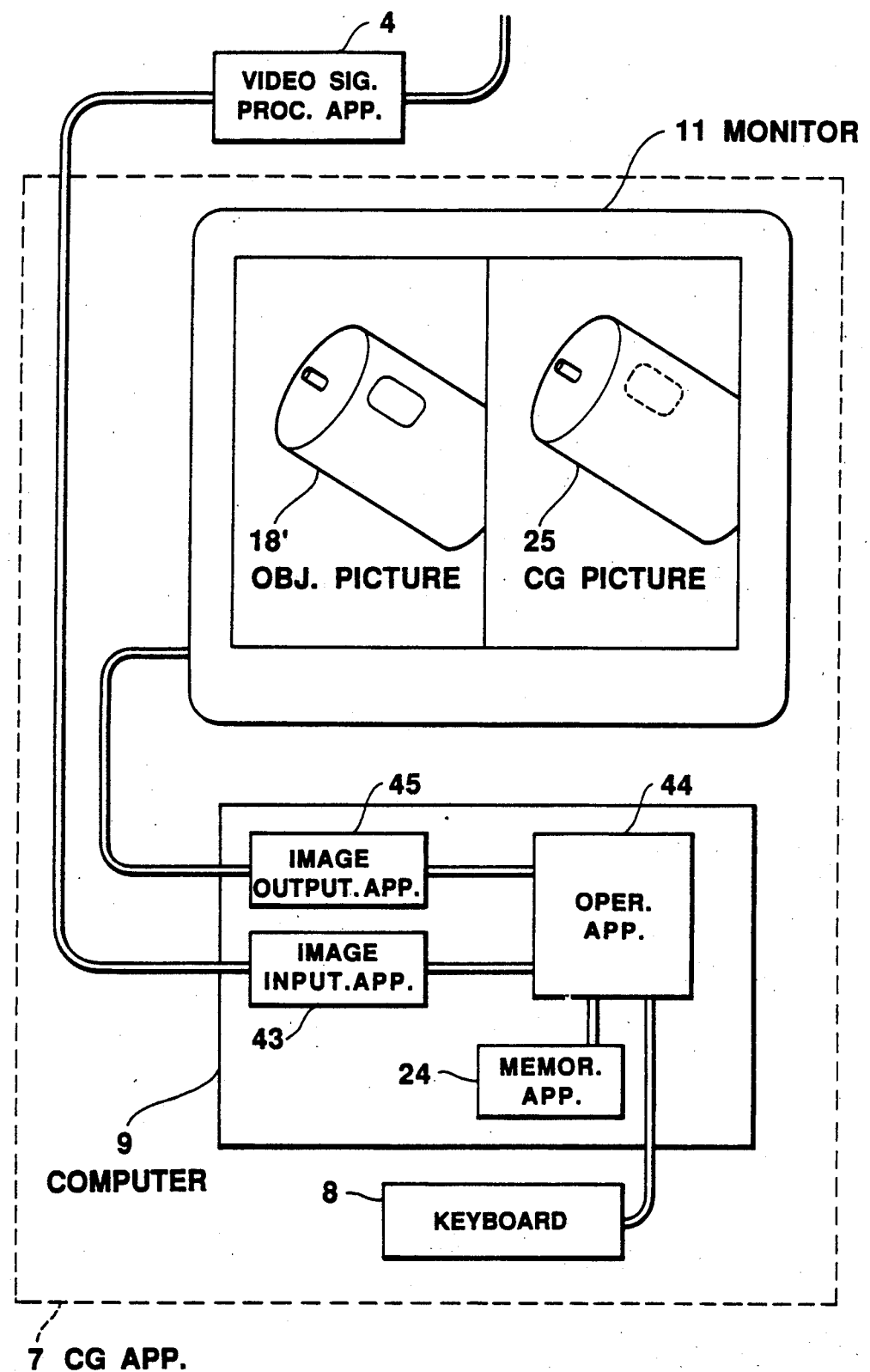

METHOD OF INSPECTING OBJECTS BY IMAGE PICKUP MEANS

BACKGROUND OF THE INVENTION

Field of the Invention and Description of the Related Art

This invention relates to a method of inspecting objects by an image pickup means according to which measurements, discoloration tests, etc. can be conducted on certain parts of an object, a picture of which is given by computer-graphics-based drawing means.

An example of an apparatus for measuring the dimensions of certain parts of an object by means of an electronic scope is disclosed in Japanese Laid-Open Patent No. 59-70903, which is shown in FIG. 1.

This prior-art apparatus employs an electronic scope 81 in which illuminating light from a light source apparatus 82 is transmitted through a light guide 83 and emitted through the end surface of a front-end section 84, thereby illuminating an object 85.

A laser-beam transmitting light guide 86 is inserted into this electronic scope 81. This laser-beam transmitting light guide 86 serves to transmit a laser beam from a laser oscillating apparatus 87 and causes it to be emitted through lenses 88, 88 provided at two branch end sections thereof. Two parallel laser beams are emitted through these branch end sections, spaced from each other by a distance d, where impinge upon the object 85, forming two laser spots 89, 89 spaced from each other by the distance d.

An optical image of the illuminated object 85 is formed on a solid image pickup element 92 by an objective lens 91 provided in the front-end section 84, the solid image pickup element 92 being arranged in the focal plane of the objective lens 91. This optical image undergoes photoelectric transfer and is supplied to a video signal processing apparatus 94 through a signal line 93. A standard video signal is generated by this video signal processing apparatus 94 and is displayed on a monitor 95. Suppose the length 1 of a part 96 to be inspected of the object 85 (e.g., a flaw on the object) is to be measured. The actual length 1 can be known from the length of the corresponding image 96' on the display and from the ratio of the actual distance d between the laser spots 89, 89 on the object to the distance between the corresponding spots 89', 89' on the display.

In the above-described conventional apparatus, measurement of length cannot be performed without using the electronic scope 81, which is equipped with the dedicated lenses 88, 88 and light guide 86 for applying the laser beam.

Because of its complicated structure, the electronic scope 81 inevitably includes a front-end section 84 with a large cross section. As a result, the front-end section 84 cannot be inserted into relatively narrow holes.

Besides, with this conventional apparatus, measurement can be conducted only where the object part to be inspected has a planar configuration which is substantially identical to the part where the laser beams are applied.

Apart from this, U.S. Pat. No. 4,725,883 discloses an optical inspection system according to which any damage, etc. to the surface of a tubular product can be detected by means of a feeler. The feeler of this system has to be engaged in a position in the vicinity of the part to be inspected, resulting in the use of this system being restricted to the inspection of the surfaces of tubular products.

A typical use of the industrial electronic scope may be the inspection of turbine blades, etc. in boilers, aircraft engines or the like. In the case of turbine blades or the like, a large number of objects having the same configuration have to be inspected. Further, since they are industrial products, their configuration and dimensions are clarified by drawings, etc.

Now, the development of minicomputers has recently made remarkable progress, making it possible to form solid bodies through computer graphics using inexpensive desk top computers.

With computer graphics, the illuminating light can be applied from an arbitrary angle to an object whose configuration and dimensions are defined, making it possible to visualize on the monitor screen how the object looks from that arbitrary angle.

When observing an object by means of an electronic scope, the distance between the scope and the object varies, so that it is not possible to measure various parts of the object from a displayed picture thereof unless a special electronic scope as described above is employed.

In the case of computer graphics, all the portions of an object, including minute ones, are perfectly controlled by a coordinate system notwithstanding the fact that the object is displayed as it looks to the eye. Accordingly, the actual length of any line segment added to a displayed computer-graphics image can be obtained by calculation. Further, the actual configuration or area of any figure added thereto can also be calculated.

In spite of this advantage, computer graphics have not been applied much to electronic scopes. Thus, no attempt has been made to measure length, etc. by means of computer graphics.

It should be further added that it is difficult to discover a flaw on an object by means of conventional methods if the object has a complicated configuration.

SUMMARY OF THE INVENTION

It is an object of this invention to provide a method of inspecting objects which utilizes the functions of computer graphics, thereby making it possible to obtain the size of a flaw or the like on a curved surface with an image pickup means.

Another object of this invention is to provide a method of inspecting objects which utilizes the functions of computer graphics, thereby making it possible to detect any discoloration in the part to be inspected of an object.

Still another object of this invention is to provide a method of inspecting objects which utilizes the functions of computer graphics, thereby making it possible for any flaw or the like in an object to be discovered with ease even if it has a complicated configuration.

This invention utilizes computer graphics in inspecting certain parts of an object by an image pickup means provided, for example, in an electronic scope. In accordance with this invention, the object is observed by an image pickup means, and, at the same time, an image simulating the observation is drawn through computer graphics. The drawing parameters are varied so as to approximate or equalize the figure on the computer-graphics display to or with the observed image, i.e., the image of the object obtained by the electronic scope or the like. Thus, even if the object has a complicated configuration, a flaw or the like on it can be discovered with ease through comparison of the two images.

Further, that part of the figure on the computer-graphics display corresponding to the part of an object picture to be inspected is specified and information on the part thus specified is utilized, thereby making it possible to measure the length of the inspected part or to examine any discoloration in it by an existing electronic scope or the like.

BRIEF DESCRIPTION OF THE DRAWINGS

FIGS. 2 to 6 are related to a first embodiment of this invention, of which:

FIG. 2 is a block diagram showing the construction of an electronic-scope apparatus used in the method according to the first embodiment;

FIG. 3 illustrates the positional parameters for displaying a computer-graphics image;

FIG. 4 illustrates the rotation-angle parameters for displaying a computer-graphics image;

FIG. 6 shows how two points corresponding to the part of the object to be inspected are specified on the picture displayed on the second monitor;

FIGS. 11a and 11b show how discoloration is examined in accordance with a third embodiment of this invention;

FIG. 12 is a block diagram showing essential parts of an electronic-scope apparatus used in the third embodiment of this invention;

FIG. 13 is a block diagram showing essential parts of an electronic-scope apparatus used in a fourth embodiment of this invention;

FIGS. 14a, 14b and 14c show the parameters used when displaying an computer-graphic image;

FIG. 15 is a block diagram showing essential parts of an image pickup apparatus used in a fifth embodiment of this invention; and FIG. 16 is a block diagram showing essential parts of a modification of the third embodiment of this invention.

DETAILED DESCRIPTION OF THE PREFERRED EMBODIMENTS

Figure 1:
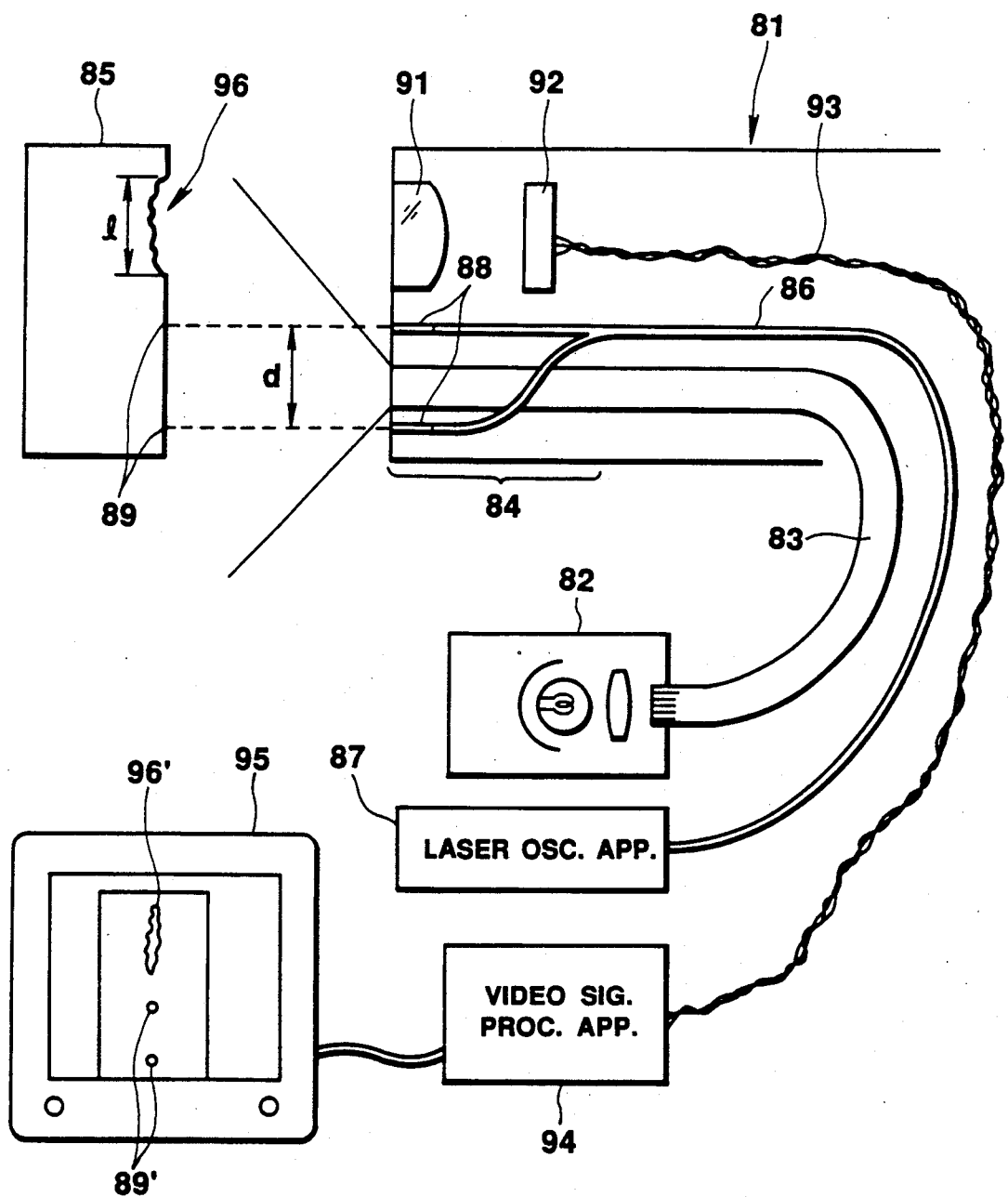
FIG. 1 is a block diagram showing the construction of a conventional measuring apparatus.
Figure 2:
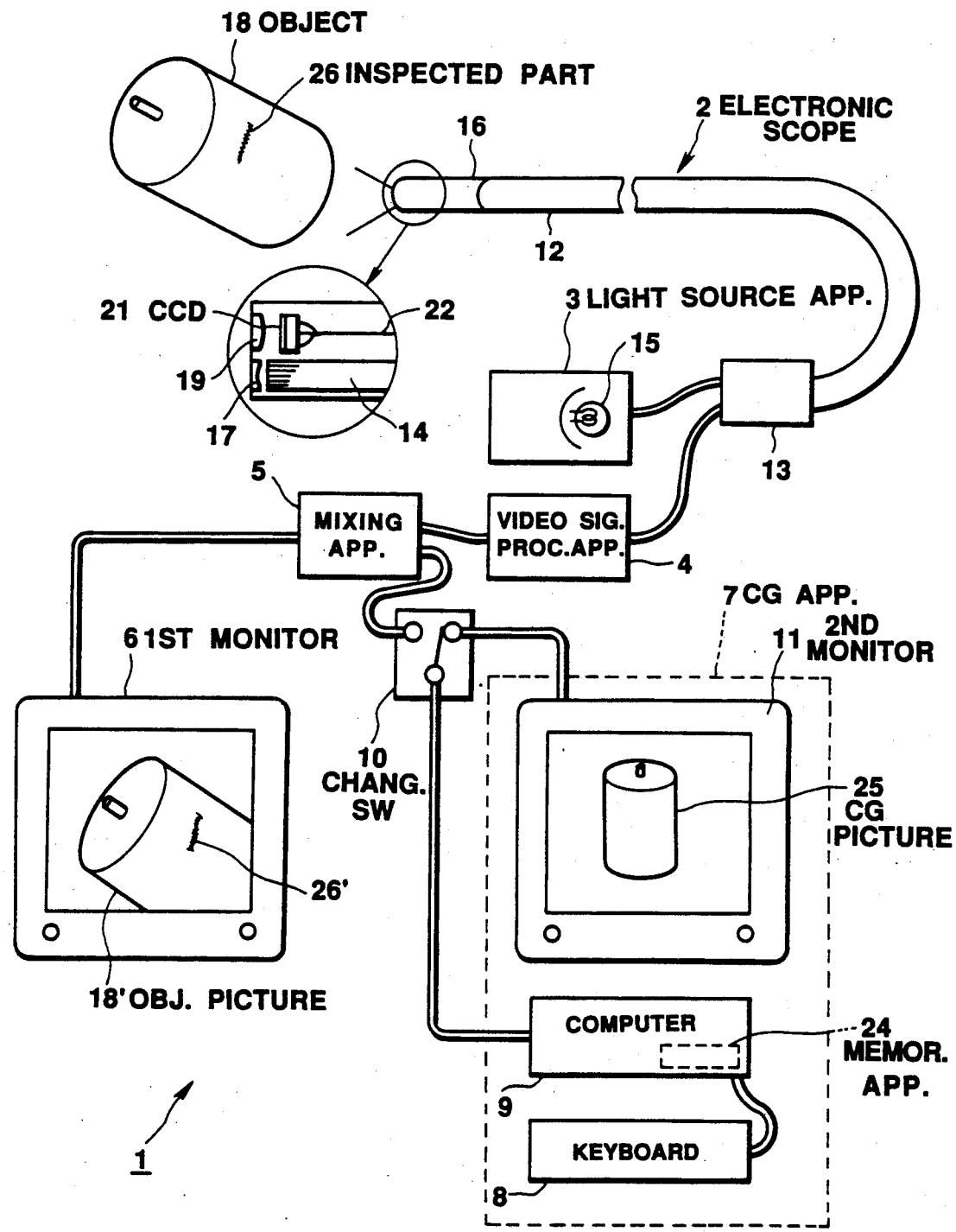

FIG. 2 shows an electronic-scope apparatus 1 in accordance with the first embodiment of this invention. The electronic-scope apparatus 1 comprises an electronic scope 2, a light source apparatus 3 for supplying illuminating light to this electronic scope 2, a video signal processing apparatus 4 for performing signal processing for the image pickup means of the electronic scope 2, a first monitor 6 for displaying a standard video signal generated in this video signal processing apparatus 4 through a mixing apparatus 5, and a computer-graphics apparatus 7.

The above computer-graphics apparatus 7 comprises a keyboard 8 for entering data such as drawing commands and drawing parameters, a computer 9 for performing calculation on the basis of the data entered through this keyboard 8 so as to generate a computer-graphics (hereinafter abbreviated as "CG") video signal, and a second monitor 11 for displaying this CG video signal through a changeover switch 10.

By appropriately manipulating the above changeover switch 10, the CG video signal output from the computer 9 can also be displayed on the first monitor 6 through the mixing apparatus 5.

The above electronic scope 2 includes an elongated insertion section 12, to the rear-end section of which an operating section 13 with a large cross-section is connected.

A light guide 14 is inserted into the insertion section 12. The rear-end section of this light guide 14 is connected to the light source apparatus 3. Illuminating light from a lamp 15 is transmitted through this light guide 14 and is emitted toward an object 18 through an illuminating lens 17 provided in the end surface of the front-end section 16.

An image of the object 18 thus illuminated is formed on a CCD 21 by an objective lens 19 provided in the front-end section 16, the CCD 21 being arranged in the focal plane of the objective lens 19. A mosaic color filter is attached to the image pickup surface of this CCD 21 so that color separation can be effected for each pixel.

The video signal undergoes photoelectric transfer in the CCD 21 and is supplied through a signal line 22 to the video signal processing apparatus 4, where it undergoes video signal processing. An object picture 18' is then displayed on the first monitor 6 through the mixing apparatus 5.

The above-mentioned computer 9 is equipped with a built-in memory apparatus 24, which consists, for example, of a floppy-apparatus or a hard-disk apparatus. Stored in this memory apparatus 24 are CG-picture drawing programs which make it possible to effect a simulation display of the object 18, which typically consists of a turbine blade or the like provided in a boiler or an engine (the object is represented, for simplification's sake, as a cylindrical body). Written to the memory apparatus 24 is data on the configuration and the dimensions of the known object 18, a three-dimensional CG picture being displayed on the second monitor 11, etc. in accordance with the dimensions written. (The memory apparatus 24 may consist of an ROM to which CG programs are written.)

The above-mentioned second monitor 11 first displays a three-dimensional CG picture 25 showing the object (which, in this case, consists of a cylindrical body) as arranged in the most standard position and as seen perspectively, etc. (see FIG. 2).

Thus, by entering through the keyboard 8 the drawing parameters, such as the direction of the object, the positional relationship between the object and the viewpoint, the field angle, and the illuminating direction, the CG picture 25 for the same object can be displayed in various ways.

Figure 3:
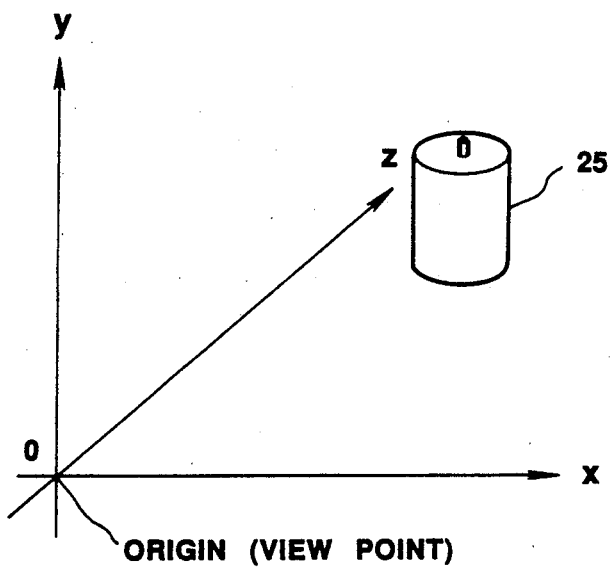

The position for the simulation display of the object can be determined, as shown in FIG. 3, by using a three-dimensional orthogonal x-, y-, z-coordinate system, with the viewpoint being regarded as its origin. By, for example, diminishing the values of the parameters x, y and z, a larger CG picture 25 can be displayed.

Figure 4:
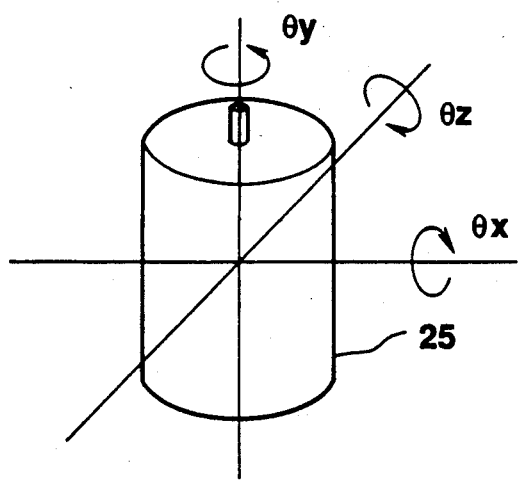

As to the direction of the object when it is simulation-displayed, it can be determined, as shown in FIG. 4, by using the three rotation angles $\theta x$, $\theta y$, and $\theta z$ about the axes passing center of the CG picture 25, set in the standard direction.

The field angle is set to be the same as that of the electronic scope 2 used.

As to the illuminating direction, a point source can be considered to exist at the same position as the viewpoint in FIG. 3 since, in the case of the electronic scope 2, the objective lens 19 is very close to the illuminating lens 17.

When the object 18 is imaged by the image pickup means of the electronic scope 2, there is of course no ascertaining from the first monitor 6 the various factors for displaying the object picture 18' in the manner as in FIG. 2, for example, the angle of inclination of the cylindrical object 18 or the distance between the object 18 and the front end of the electronic scope.

However, by varying the values of the above-mentioned six parameters x, y, z, $\theta x$, $\theta y$, and $\theta z$, the CG picture 25 (given as a simulation display of the object 18) can be arbitrarily directed and positioned. Thus, the CG picture 25 of the second monitor 11 shown in FIG. 5b can be displayed in such a manner that it is completely, or at least substantially, identical to the object picture 18' on the first monitor 6 shown in FIG. 5a.

The process of thus bringing the CG picture 25 into concordance with the object picture 18' can be executed by the operator through manipulation of the keyboard 8.

The keyboard 8 includes keys for augmenting or reducing the respective values of the six parameters x, y, z, $\theta x$, $\theta y$, and $\theta z$. The operator can bring the CG picture 25 on the second monitor 11 from the drawing (display) condition shown in FIG. 2 to the condition shown in FIG. 5b, i.e., bring it into concordance with the object picture 18' on the first monitor 6, which represents the observation image obtained by the electronic scope. (In some cases, approximation to the observation image suffices).

In this process, the operator may manipulate the changeover switch 10 to mix the image obtained by the electronic scope 2 with the CG picture 25 by means of the mixing apparatus 5, outputting them as an image signal to the first monitor 6 and displaying the two images on the first monitor 6, with one being superimposed on the other. Thus, the operation of bringing the two images into concordance with each other and the judgment on the concordance can be effected with ease.

By thus bringing the two images into concordance with each other, the existence of any flaw on the object can be easily noticed through a comparison of them, even if the object picture 18' has a complicated configuration.

Figure 5A:
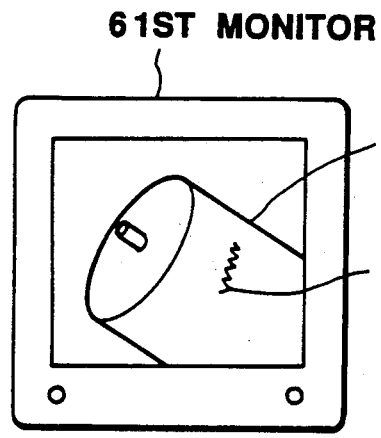
FIGS. 5a and 5b illustrate the case where a computer-graphics image displayed on a second monitor is brought into concordance with an object picture displayed on a first monitor.
Figure 5B:
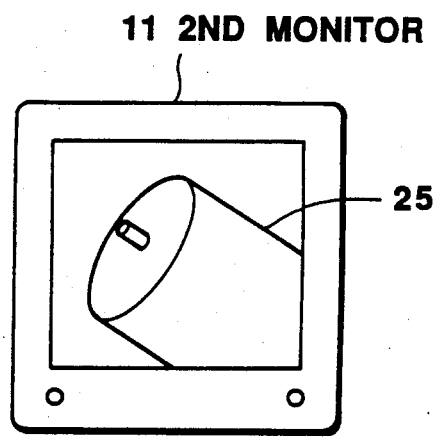

After performing the process of bringing the images given on the first and second monitors 6 and 11 into concordance with each other as shown in FIGS. 5a and 5b, the length of the flaw, which constitutes the inspected part 26 of the object 18, can be measured in the following manner.

As shown in FIGS. 5a and 5b, the image 26' of the inspected part 26 is only displayed on the first monitor 6 even when they have been brought into concordance with each other.

Figure 6:
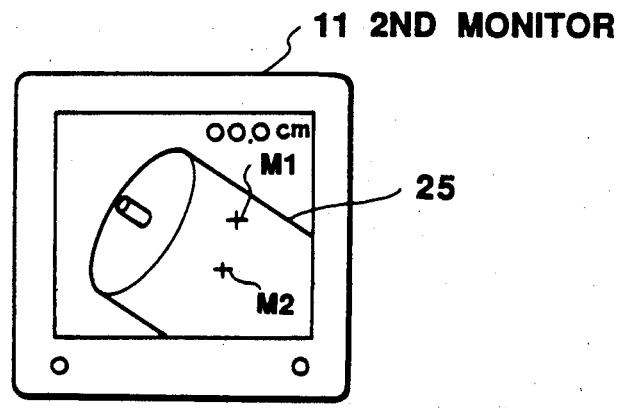

Then, the operator manipulates the keyboard 8 to move the cursor, specifying on the CG picture displayed on the second monitor 11 the section corresponding to the flaw by adding marks M1 and M2 to the display on the second monitor, as shown in FIG. 6.

With the electronic-scope image displayed on the first monitor 6 alone, the length of the flaw cannot be known. On the other hand, the simulation image of the cylindrical object 18 displayed on the second monitor 11 is an image whose position and direction are all numerically controlled for display on the basis of the data on the configuration and the dimensions of the cylindrical object, as stated above. Accordingly, the coordinates of the marks M1 and M2 telling the positions where they are added can be known with ease. Thus, the actual distance between the marks M1 and M2 can be easily calculated. The distance between the marks M1 and M2, that is, the length of the flaw to be measured, which constitutes the inspected part 26, is displayed, for example, on the second monitor shown in FIG. 6, in the form of a numerical value.

In this way, dimensions of the inspected part, for example, the length thereof, can be obtained.

The above-described first embodiment is advantageous in that measurement can be performed without using an electronic scope equipped with a special construction as in the prior-art example, and that the diameter of the insertion section can be accordingly smaller, which enables it to be inserted into a thin hole.

Furthermore, the object is not restricted to a plane figure but may be any solid body such as a cylindrical one, which can be allows not only observation but also measurement.

In addition, as is apparent from FIGS. 5a and 5b, it is not necessary for the object picture 18' and the CG picture 25 given on the first and second monitors 6 and 11 to represent the entire object; a partial display is enough as long as it indicates the concordance in configuration between the two. Further, the CG picture 25 displayed on the second monitor 11 may, in this embodiment, be a line-drawing display (wire-frame model) representing the outward view only.

While in the example shown in FIG. 6 solely the two points M1 and M2 are specified, it is also possible to further specify points between M1 and M2, measuring the length of the segment on which these points lie.

Figure 7:
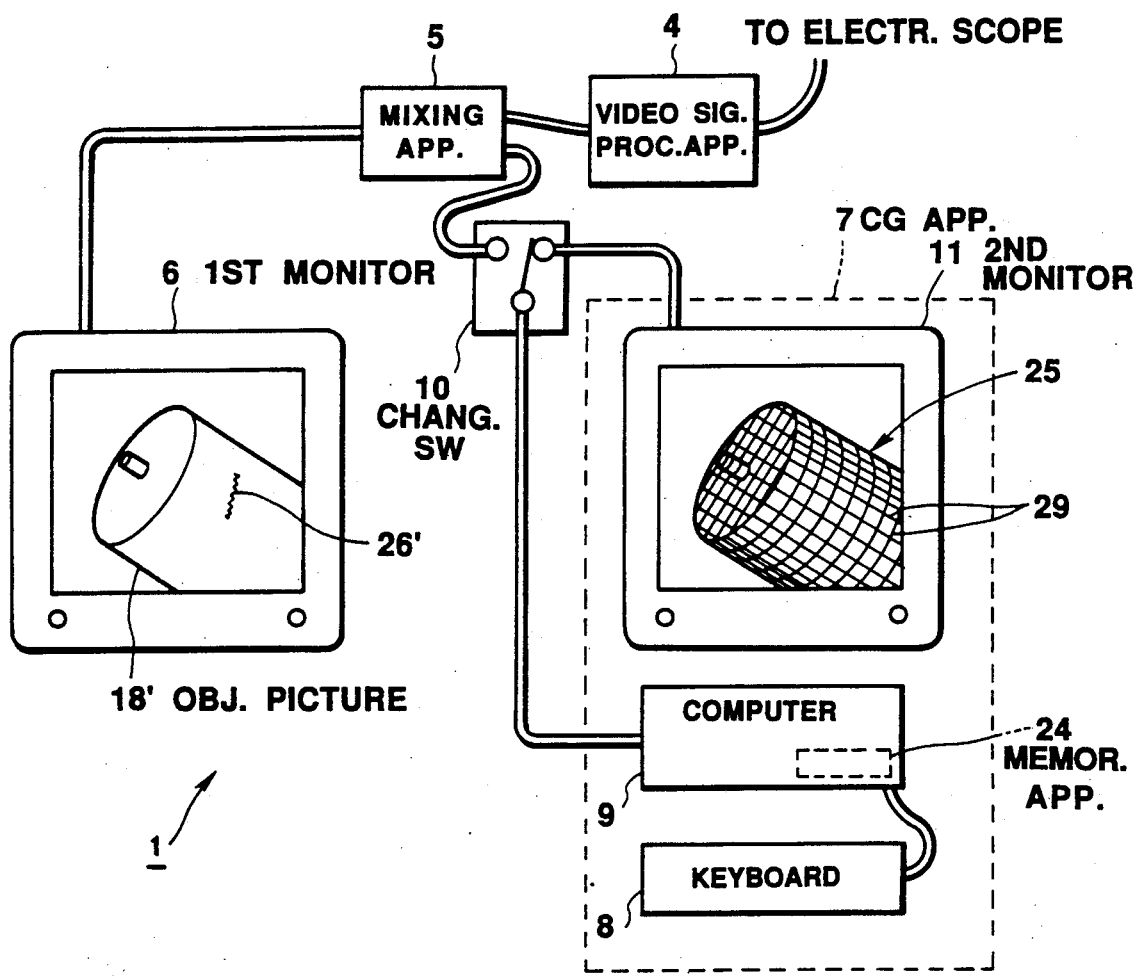
FIG. 7 is a block diagram showing essential parts of an electronic-scope apparatus related to a modification of the first embodiment.

FIG. 7 shows essential parts of an apparatus in accordance with a modification of the first embodiment of this invention.

In this modification, the computer 9 of the first embodiment is further equipped with a function of displaying a scale on the CG picture.

When the object picture 18' and the CG picture 25 have been brought into concordance with each other, as shown in FIGS. 5a and 5b, the operator manipulates the keyboard 8 to display on the CG picture 25 a standard scale, for example, a lattice scale of 1 cm pitch 29. As shown in FIG. 7, the drawing of the object is made such that it shows this scale 29 as provided on the surface of the object represented by the CG picture 25. The operator then manipulates the changeover switch 10, shown in FIG. 7, to output the scaled CG picture to the first monitor 6 through the mixing apparatus 5, displaying on the first monitor 6 the object picture 18' and the scaled CG picture, with one being superimposed on the other, as shown in FIG. 8.

Figure 8:
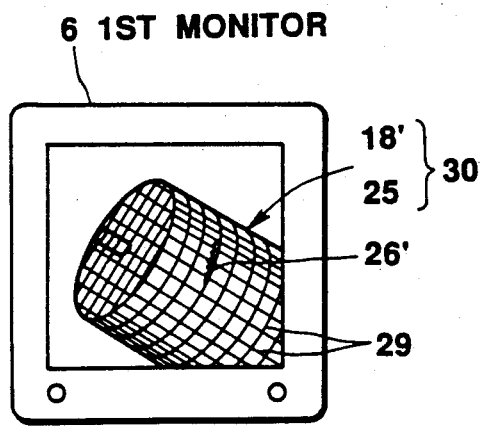
FIG. 8 shows how an object picture and a computer graphics image are displayed on the first monitor, with one being superimposed on the other.

Thus, the picture 30 displayed on the first monitor 6 of FIG. 8 is a synthesized image of the object picture 18' obtained by the image pickup means and the CG picture 25 which has been brought into concordance with it.

In this picture 30, the image 26' of the inspected part is an image obtained by the image pickup means.

On the other hand, the CG picture with the lattice scale 29 is a CG picture drawn by means of the computer 9.

In computer graphics, it is easy to generate a lattice scale along the surface of an arbitrary object.

When the picture of FIG. 8 has been thus displayed, it is easy for anyone to know the length of the inspected part 26 by comparing it with the 1 cm-pitch lattice scale.

FIG. 9 shows the way in which the area of the inspected part 31 is measured in accordance with the method of the second embodiment of this invention.

Figure 9A:
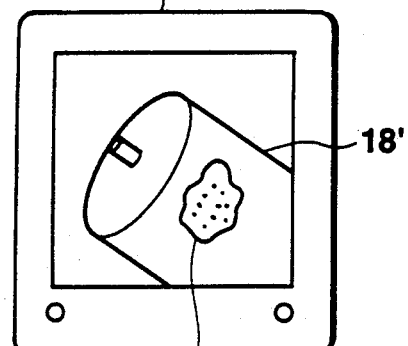
FIGS. 9a and 9b show how an area is measured in accordance with a second embodiment of this invention.

In this second embodiment, the object 18 has a plane rust portion, as indicated in the display on the first monitor 6 of FIG. 9a. Here, the area of this rust portion, which constitutes the inspected part 31, is to be measured. In the second embodiment, the apparatus shown in FIG. 2 may be used.

As stated with reference to the first embodiment, the CG picture 25 displayed on the second monitor 11 is brought into concordance with the object picture 18' displayed on the first monitor 6.

Figure 9B:
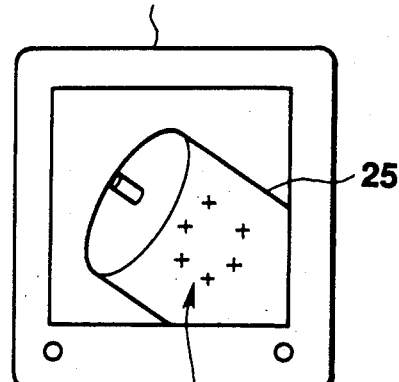

Next, in correspondence with the rust portion, marks M1 to M6, for example, are added to the CG picture 25, as shown in FIG. 9b. Since the x-, y-, and z-coordinates of the marks M1 to M6 are obvious on the CG picture, the area of the portion surrounded by the marks M1 to M6, i.e., the actual area of the rust portion, can be calculated and displayed, for example, on the screen of the second monitor 11 (The manner of display is not shown here).

Also in this case, the measurement can be effected with accuracy even when the inspected part 31 does not have a plane configuration.

Figure 10A:
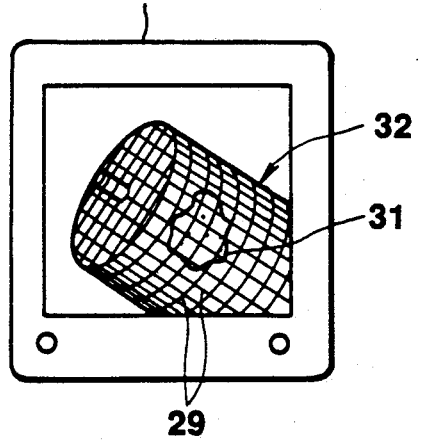
FIGS. 10a and 10b show an image obtained in accordance with a modification of the second embodiment.
Figure 10B:
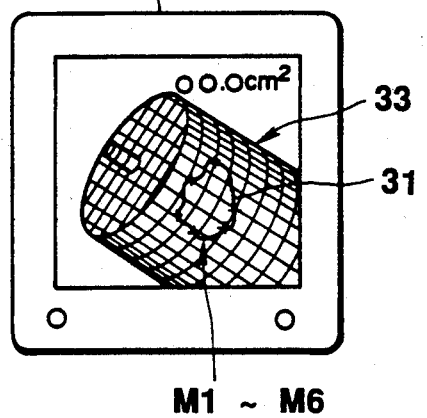

FIGS. 10a and 10b shows a picture obtained in accordance with a modification of the second embodiment of this invention.

As stated with reference to the modification of the first embodiment, a lattice scale 29 is displayed on the CG picture 25 after it has been brought into concordance with the object image 18'. Afterwards, the changeover switch 10 is manipulated to mix the CG picture 25 with the object picture 18' through the mixing apparatus 5, displaying the synthesized picture thus obtained on the first monitor 6 as a picture 32, which is shown in FIG. 10a. By comparing, from this picture, the image of the inspected part 31 with the lattice scale 29, anyone can approximately assess the area of the inspected part 31.

Further, by adding the marks M1 to M6 to the picture 32 of FIG. 10a, a picture 33 as shown in FIG. 10b is obtained. The area of the section surrounded by these marks M1 to M6 is calculated by the computer 9 and given on the display, as shown in FIG. 10b.

The respective positions of the marks M1 to M6 can be determined with the CG picture mixed with the object picture and with the scale 29 displayed, so that the measurement of the area can be conducted with high accuracy. By augmenting the number of marks, for example, the area measurement can be conducted with a still higher accuracy.

FIGS. 11a and 11b illustrate the method in accordance with the third embodiment of this invention.

Here, an inspected part 41 of the object is checked to see whether it has suffered a change in quality on account of heat. If the quality of this part 41 has been changed, its color must have changed with respect to the other parts. Accordingly, a judgment as to whether or not the quality of this part has changed can be made checking its color.

However, it should be noted here that the illuminating light is supplied to the object in a particular direction, so that, even when the color of the object is uniform throughout its surface, the surface brightness can be different in different sections of the surface. Thus, with the object image 18' displayed on the first monitor 6 of FIG. 11a, it is a very difficult to make a judgment as to whether or not the inspected part 41 has a color different from the color of the other parts of the object. Such a judgment can only be made by those highly skilled in the art.

By applying this embodiment to a case like this, the above judgment can be made with ease and reliably. In the case of this embodiment, not only the data on the configuration and the dimensions of the cylindrical object 18 but also the data on its surface color and its reflectance is previously supplied to the computer 9. Thus, the CG function employed here is not that of displaying the object 18 in the form of a line drawing but that of displaying the surface conditions of the object 18, including the reflection with respect to the illuminating light, is used as the CG function. This CG function makes it possible to display on the second monitor of FIG. 11b a CG picture 25 which is substantially identical to the picture obtained by observing the cylindrical object 18 with the electronic scope 2 when the quality of the object 18 has not been changed by heat.

Thus, instead of comparing the color of the inspected part 41 of the object 18 as displayed on the first monitor 6 with the color of the other parts thereof, the operator can compare the corresponding section A on the picture displayed on the second monitor 11, thereby distinctly making a judgment as to whether or not the inspected part 41 has suffered discoloration. It is easy for the operator to perform this comparison visually. However, by employing some equipment for hue measurement, the judgment can be made more easily and more objectively.

It is also possible, in the example shown in FIG. 2, to provide a means for delivering the object picture 18' to the computer 9, displaying the delivered image on the second monitor 11, specifying the inspected part 41 through the keyboard 8, performing image signal subtraction between this specified section in the object image 18' and that section A on the CG picture 25 which corresponds the inspected part of the object picture 18' (The subtraction is performed for luminance and color-difference signals, respectively, or for color-difference-signal components only), and to provide a display on the second monitor 11 through the difference signal indicating whether or not there has been a hue change. In this case, the absence of hue change indicates a black level, whereas, if there has been some hue change, the residual hue-change quantity is displayed.

FIG. 12 shows the construction of an apparatus 42 equipped with a function as described above.

The apparatus shown includes a computer 9 which is composed of an image input apparatus 43 to which an output signal from a video signal processing apparatus 4 is supplied, an operating apparatus 44 for performing the operations of digital image data and CG image data entered through the image input apparatus 43, an image output apparatus 45 for outputting the picture data generated through the operations of the operating apparatus 44, and a memory apparatus 24.

An image pickup signal from the electronic scope 2 shown in FIG. 2 is supplied to the video-signal processing apparatus 4. This image pickup signal is processed into a standard video signal and output to the first monitor 6, which normally displays the object picture 18'. Further, this video signal is delivered to the image input apparatus 43 in the computer 9 and is transformed to digital-image data before it is supplied to the operating apparatus 44.

This operating apparatus 44 performs, for each pixel, subtraction between object-picture data from the image input apparatus 43 and the CG-picture data prepared in the operating apparatus 44 (for those sections specified through the keyboard 8 or for the entire object picture 18'), and outputs the picture data obtained through the subtraction to the image output apparatus 45. In this case, the subtraction results for those sections of the object picture 18' which exhibit the same color and the same luminance as the corresponding sections of the CG picture are 0, so that they are displayed on the second monitor 11 in black.

On the other hand, the subtraction results for those sections of the object picture 18' which exhibit different colors and different luminances from those of the corresponding sections of the CG picture are not 0, so that the display on the second monitor 11 is made in a color other than black. Thus, by checking on this point, the operator can easily detect any portion of the object which has been, for example, discolored by heat.

The operating apparatus 44 may transfer the object-picture data obtained by the image input apparatus 43 without performing any operation on it. In that case, the second monitor 11 displays the same object image as on the first monitor 6.

The operating apparatus 44 may also perform addition between the CG picture data prepared therein and the object picture data obtained by the image input apparatus 43 for each pixel and transmit the result to the image output apparatus 45. In that case, the second monitor 11 displays an image made by synthesizing the object picture with the CG picture.

FIG. 13 shows the construction of an electronic-scope apparatus 51 in accordance with the fourth embodiment of this invention.

This apparatus 51 employs, instead of the electronic scope 2 shown in FIG. 2, a fiber scope 52 and a TV camera 54 connected to the an eye-piece section 53 of the fiber scope.

The above TV camera 54 has a built-in video signal processing apparatus 4, through which an image taken is converted to a standard video signal to be supplied to a measurement station 55. Part of the signal supplied to the measurement station 55 is output to a monitor 57 through a changeover switch 56. The rest is output to the monitor 57 through a mixing apparatus 5 and the changeover switch 56.

Part of the output signal from a computer 9 is output to the monitor 57 through the changeover switch 56. The rest is output to the monitor 57 through the mixing apparatus 5 and the changeover switch 56. By thus passing the signal through this mixing apparatus 5, the object picture 18' from the TV camera 54 is mixed with the CG picture from the computer 9, both being displayed on the common monitor 57, with one superimposed on the other.

The outward appearance of the above fiber scope 52 resembles the electronic scope 2. The fiber scope 52 has an operating section 61 which is formed at the rear end of its elongated insertion section 60.

A light guide 62 is inserted into the above insertion section 60. By connecting a light guide cable 63 extending beyond the operating section 61 to a light source apparatus 3, illuminating light is supplied from a lamp 15. The illuminating light, transmitted through this light guide 62, is emitted toward the object 18 through an illuminating lens 64. An objective lens 66 provided at the front end 65 of the insertion section 61 causes an image of the object to be formed on an image guide 67 arranged in its focal plane, the image being transmitted to the end surface on the side of the eye-piece section 53.

The TV camera 54 has a built-in image forming lens 68, which causes an optical image transmitted through the image guide 67 to be formed on a CCD 69. A mosaic color filter is attached to the imaging surface of this CCD 69.

Having undergone photoelectric transfer in this CCD 69, the signal is converted to a standard video signal by the built-in video signal processing apparatus 4 and is supplied to the measurement station 55 through a signal cable 70.

In this apparatus 51, all the components are put together in a case as the measurement station 55 except for the fiber scope 52, the TV camera 54, and the light source apparatus 3, which is convenient when the apparatus is used while being moved.

Furthermore, to diminish the apparatus size, a single monitor 57 is used, which allows display of any of the three types of images: an electronic-scope image, a CG picture, and a synthesized image of the electronic-scope image and the CG picture by manipulating the changeover switch 56.

The compute 9 of this apparatus is equipped with a floppy disk apparatus 71. As stated above, a turbine blade or the like, which is a typical object for the industrial electronic scope, is often designed through CAD (computer aided design).

In CAD, the coordinates of an object is controlled in detail by numerical values. In a CAD apparatus, data on the coordinates of an object is recorded on a floppy disk 72, which is attached to the floppy disk apparatus 71 of the measurement station 55 of this embodiment, thereby enabling the operator to utilize the data on the configuration and the dimensions of the object when preparing a CG picture without performing any input operation. In the example shown in FIG. 13, a mouse 73 is used instead of the keyboard 8 of FIG. 2.

The mouse 73 includes two built-in rotary encoders arranged at right angles to each other. By moving the mouse 73 on the desk or the like, the operator can supply data on, for example, two variables x and y, to the computer 9. The mouse 73 is further equipped with two or so push-button switches, the computer 9 also sensing them when the operator depresses these push-button switches.

In the first embodiment, the operator enters the coordinates: x, y and z for determining the position of an object and the coordinates: $\theta x$, $\theta y$ and $\theta z$ for determining its direction through the keyboard 8. In this embodiment, these coordinates are entered by means of the mouse 73, which helps to improve the operability.

The mouse 73 allows data on two variables to be simultaneously entered, so that, as shown in FIGS. 14a, 14b and 14c, all the parameters can be entered by switching between the three modes: (1) vertical and horizontal movements xy, (2) longitudinal movement z and horizontal rotation $\theta y$ and (3) longitudinal inclination $\theta x$ and lateral inclination $\theta z$. Instead of the mouse 73, a joy stick, a track ball, a dial, etc. may be employed.

As in the modifications of the first and second embodiments, a scale may be displayed in the embodiment shown in FIG. 13.

With the apparatus 42 shown in FIG. 12, it is possible to automatize the process of bringing the CG picture into concordance with the object picture.

In the embodiments described above, the operator can vary the parameters X, Y, Z, $\theta x$, $\theta y$ and $\theta z$ by manipulating the keyboard 8 or the mouse 73 so as to bring the CG picture into concordance with the object picture In the apparatus shown in FIG. 12, the operating apparatus 44 can perform differential operation using the object picture data obtained by the image input apparatus 43, thereby extracting the contour of the object picture. The operating apparatus 44 can vary all the parameters X, Y, Z, $\theta x$, $\theta y$ and $\theta z$ in such a manner that this contour is caused to approximate to the CG picture, finally bringing the into concordance with each other. That is, the process of bringing the CG picture into concordance with the object picture is effected with the operator performing no operation at all, a feature which is very convenient.

In the first embodiment, the marks M1 and M2 are added to the image displayed on the second monitor 11. In this embodiment, this operation can also be conducted using the mouse 73. Further, instead of the mouse 73, a light pen can be conveniently employed.

In the above-described embodiments, an electronic scope is used. However, it should be added that a micro TV camera has recently been developed, which, like the electronic scope, can be inserted into a pipe or a narrow hole for the purpose of inspecting the inside of an object. That is, it is used in the same manner as the industrial electronic scope.

The present invention can also be applied to the case where such a micro TV camera is used. Accordingly, an explanation in this regard will be given with reference to FIG. 15. FIG. 15 shows an image pickup apparatus 170 which includes a TV camera 171, which, like the electronic scope 2, has an objective lens 19 and a CCD 21 arranged in the focal plane 19 of the CCD 21. This TV camera 171 further includes a lamp 172 arranged adjacent to the objective lens 19 and adapted to emit illuminating light.

The above-mentioned lamp 172 is connected to a video signal processing apparatus 4 through a supply line 174 inserted into a camera cable 173. When lamp-lighting power is supplied from a power source (not shown) provided in this video signal processing apparatus 4, the lamp 172 comes on to illuminate the object 18. The objective lens 19 causes an image of the object 18 to be formed on the CCD 21. The image is picked up by the CCD 21 and is transmitted as an electrical signal through the camera cable 173 to the video signal processing apparatus 4, which processes this signal to convert it to a standard video signal before outputting it. Otherwise, the construction of this apparatus the same as that shown in FIG. 2. Its operation is the same, too.

It is obvious that, also in this image pickup apparatus 170, a scale can be added to the CG picture and that the object picture and the scaled CG picture can be mixed with each other and displayed on the first monitor 6.

Instead of using two monitors 6 and 11, a construction using a single monitor 57, as shown in FIG. 13, may be employed.

It is also possible to separately display the two pictures on a single monitor 57, as shown in FIG. 16.

Such an apparatus can be realized by using the apparatus 42 shown in FIG. 12. The video signal output from the video signal processing apparatus 4 is supplied to the image input apparatus 43 in the computer 9 and is delivered to the operating apparatus 44 after being converted to a digital image signal. This operating apparatus 44 mixes the CG picture prepared therein with the object picture entered through the image input apparatus 43 and transmits them to the monitor 11 through the image output apparatus 45, separately displaying the two pictures on the monitor screen, as shown in FIG. 16.

By watching the two pictures thus displayed on the monitor 11, the operator can easily detect any portion of the object which has been, for example, discolored by heat.

Further, by partially combining the above-described embodiments with each other, different embodiments may be constructed.

In the field of medical instruments, a simulation display of an organ or the like which is being observed can be realized by entering data on the configuration, and the dimensions thereof through an X-ray CT scanner, etc., the simulation display being utilized in, for example, measuring the size of the inspected portion of the organ or the like.

Thus, the present invention utilizes functions of computer graphics with a view to effecting simulation display of an object which is being observed by an image pickup means such as an electronic scope, performing inspecting operations such as the measurement of the length, area, etc, of an inspected part of the object or the examination of any discoloration thereof by using data on the portion of the computer-graphics image corresponding to the inspected part, thus allowing existing image pickup means such as an electronic scope to be used.

While the invention has been described in its preferred embodiments, it is to be understood that the words which have been used are words of description rather than limitation and that changes within the scope of appended claims may be made without departing from the true scope and spirit of the invention in its broader aspects.

What is claimed is:

1. A method of inspecting objects by an image pickup means, comprising:
   a first process in which an object picture obtained by imaging an object by an image pickup means is displayed on a screen of a monitor;
   a second process in which a computer-graphics picture simulating said object is displayed on the screen of said monitor or a screen of another monitor; and
   a third process in which said computer-graphics picture is approximated to said object picture by varying drawing parameters used in said computer-graphics picture.

2. A method as claimed in claim 1, further comprising a fourth process following said third process, said fourth process consisting in outputting information on that portion of said computer-graphics picture corresponding to an inspected part in said object picture, information on said inspected part being collected using the information obtained through said fourth process.

3. A method as claimed in claim 1, further comprising a scale display process in which a scale is displayed on said computer-graphics picture, length/area measurement on said inspected part being made possible by scale information provided through said scale display process.

4. A method as claimed in claim 1, 2 or 3, wherein said first process includes the operation of displaying on the screen of said monitor a standard video signal generated by signal-processing by a signal processing means a video signal of said object after it has undergone photoelectric transfer by said image pickup means.

5. A method as claimed in claim 1, 2 or 3, wherein said image pickup means includes an objective lens adapted to form an optical image of said object and a solid state imaging device arranged in a focal plane of said objective lens.

6. A method as claimed in claim 1, 2 or 3, wherein said image pickup means includes an objective lens adapted to form an optical image of said object, a fiber scope one end of which is arranged in a focal plane of said objective lens and the other end of which has an image guide adapted to transmit optical images, and a TV camera attached to an eye-piece section of said fiber scope and equipped with a built-in solid state imaging device.

7. A method as claimed in claim 1, 2, or 3, wherein said second process includes the operation of supplying a computer with information on at least the outer configuration and the size of said object and simulation-displaying on a monitor screen a computer-graphics picture representing said object as observed from a certain viewpoint.

8. A method as claimed in claim 7, wherein said computer-graphics picture displayed in said second process is a wire-frame picture.

9. A method as claimed in claim 7, wherein said information on the outer configuration and the size of said object is supplied to the computer, simulation-displaying on a monitor screen a computer-graphics picture corresponding to said object as observed from a certain viewpoint.

10. A method as claimed in claim 7, wherein said information on the outer configuration and the size of said object can be stored and read in and from a storage means.

11. A method as claimed in claim 7, wherein said third process includes the operation of approximating to said object picture of said first process a computer-graphics picture obtained by varying drawing parameters for a computer-graphics picture corresponding to the object as observed from a certain viewpoint, said drawing parameters consisting of the three-dimensional positional parameters x, y and z of said viewpoint and rotation-angle parameters $\theta x$, $\theta y$ and $\theta z$ determining the direction in which the object is three-dimensionally observed.

12. A method as claimed in claim 11, wherein an illuminating light parameter determining the direction of an illuminating light for illuminating a computer-graphics picture corresponding to the object can be entered as one of said drawing parameters.

13. A method as claimed in claim 2, wherein said fourth process includes the step of specifying an arbitrary portion of the computer-graphics picture after said third process, information on said computer-graphics picture corresponding to the arbitrary portion specified being output from a computer, thereby making it possible to obtain information on that part of the object requiring inspection and corresponding to said arbitrary portion.

14. A method as claimed in claim 13, further comprising a length-information output process in which calculation is further performed on the information on the computer-graphics picture corresponding to said specified arbitrary portion, thereby causing length information to be output.

15. A method as claimed in claim 13, further comprising an area-information output process in which calculation is further performed on the information on the computer-graphics picture corresponding to said specified arbitrary portion, thereby causing area information to be output.

16. A method as claimed in claim 2 or 3, wherein the means for varying drawing parameters in said third process consists of at least one of the following: a keyboard, a mouse, a joy stick, a dial, and a track ball.

17. A method as claimed in claim 13, wherein the means for specifying an arbitrary portion in said computer-graphics picture consists of at least one of the following: a keyboard, a mouse, a light pen, a joy stick, a dial, and a track ball.

18. A method as claimed in claim 1, 2 or 3, wherein said second process includes the operation of supplying a computer with information on the color and the reflectance of the surface of a figure in a computer-graphics picture corresponding to the object and displaying the information in the form of a color picture.

19. A method as claimed in claim 18, wherein subtraction is performed between picture data on said computer-graphics picture and picture data on said object picture, picture data obtained through the subtraction being displayed on said monitor or another monitor.

20. A method as claimed in claim 1, 2 or 3, wherein a mixing means for mixing said computer-graphics picture after said third process with said object picture is employed, said computer-graphics picture and said object picture being displayed on the same monitor, with one being superimposed on the other.

21. A method as claimed in claim 1, 2 or 3, wherein said third process includes the operation of extracting the contour of said object image, automatically determining said drawing parameters by performing calculation in such a manner that the contour of said computer-graphics picture is brought into concordance with this contour.

22. A method as claimed in claim 3, wherein said scale display process includes the operation of displaying a lattice-like scale of a reference length along the outer surface of said computer-graphics picture.

23. A method as claimed in claim 3, wherein a mixing means for mixing said computer-graphics picture after said third process with said object picture is employed, said computer-graphics picture and said object picture being separately displayed on the same monitor.

24. A method as claimed in claim 1, 2 or 3, wherein said computer-graphics picture or said object picture displayed in said second process is a picture corresponding to a part of the entire object.

25. A method of inspecting objects by means of an electronic scope, comprising:
   a first process in which an object picture obtained by imaging an object by an image pickup means of the electronic scope is displayed on a screen of a monitor;
   a second process in which a computer-graphics picture simulating said object is displayed on the screen of said monitor or a screen of another monitor; and
   a third process in which drawing parameters for said computer-graphics picture are varied, thereby approximating said computer-graphics picture to said object picture.

26. A method as claimed in claim 25, further comprising a fourth process in which information on that portion of said computer-graphics picture after said third process which corresponds to an inspected part of said object picture is output.

27. An inspection system using computer-graphics means, comprising:
   an illuminating-light emitting means for emitting illuminating light for illuminating an object;
   an image pickup means composed of an objective optical system adapted to form an optical image of said object illuminated by said illuminating light and an imaging device adapted to effect photoelectric transfer of the optical image;
   a signal processing means adapted to generate a video signal out of an output signal from said imaging device;
   a monitor means for displaying an object picture from said video signal output from said signal processing means;
   a computer-graphics means capable of displaying a computer-graphics picture corresponding to a solid figure simulating said object by entering information data on at least the configuration of said object and capable of displaying said solid figure as rotated by an arbitrary angle, moved parallel and enlarged/reduced by entering drawing parameters; and
   a drawing parameter entering means for entering drawing parameters for displaying on said computer-graphics means a picture approximated to said object picture.

28. A system as claimed in claim 27, wherein said computer-graphics means includes a function of specifying that portion of said computer-graphics picture approximated to said object picture which corresponds to an inspected part of said object picture, thereby outputting information on said portion.

* * * * *